United States Patent
Berkus et al.

(10) Patent No.: US 9,848,835 B2
(45) Date of Patent: Dec. 26, 2017

(54) VARIABLE-SPEED COMPUTED TOMOGRAPHY SCANNING

(75) Inventors: Timo Berkus, Ennetbaden (CH); Xiu Ting Zhuang, Baden (CH); Andres Graf, Oberwil (CH); Markus Oelhafen, Rohr (CH); Patrik Kunz, Baden (CH)

(73) Assignee: Varian Medical Systems International AG, Cham (CH)

( * ) Notice: Subject to any disclaimer, the term of this patent is extended or adjusted under 35 U.S.C. 154(b) by 628 days.

(21) Appl. No.: 12/857,178

(22) Filed: Aug. 16, 2010

(65) Prior Publication Data
US 2012/0039433 A1    Feb. 16, 2012

(51) Int. Cl.
 *A61B 6/03* (2006.01)
 *A61B 5/113* (2006.01)
 *A61B 6/00* (2006.01)
 *A61B 5/11* (2006.01)

(52) U.S. Cl.
 CPC .............. *A61B 6/032* (2013.01); *A61B 5/113* (2013.01); *A61B 6/541* (2013.01); *A61B 5/1127* (2013.01)

(58) Field of Classification Search
 CPC ................................ A61B 6/032; A61B 6/541
 USPC .................................................. 378/8, 95, 62
 See application file for complete search history.

(56) References Cited

U.S. PATENT DOCUMENTS

| | | | |
|---|---|---|---|
| 6,233,308 B1 * | 5/2001 | Hsieh | 378/62 |
| 6,269,140 B1 * | 7/2001 | Takagi et al. | 378/8 |
| 6,370,217 B1 * | 4/2002 | Hu et al. | 378/8 |
| 6,574,500 B2 | 6/2003 | Keren | 600/431 |
| 6,628,742 B2 * | 9/2003 | Pan | A61B 6/032 378/4 |
| 6,865,248 B1 * | 3/2005 | Rasche et al. | 378/8 |
| 7,177,386 B2 | 2/2007 | Mostafavi et al. | |
| 7,221,733 B1 * | 5/2007 | Takai et al. | 378/65 |
| 7,376,214 B2 * | 5/2008 | Klingenbeck-Regn | 378/8 |
| 7,496,175 B2 * | 2/2009 | Sakaguchi et al. | 378/95 |
| 7,711,080 B2 * | 5/2010 | Mori | A61B 6/032 378/15 |
| 7,924,971 B2 * | 4/2011 | Knox et al. | 378/8 |
| 8,005,284 B2 * | 8/2011 | Sakaguchi et al. | 382/131 |
| 8,611,987 B2 * | 12/2013 | Allmendinger | A61B 5/0456 378/11 |
| 9,084,542 B2 * | 7/2015 | Bouhnik | A61B 6/032 |

* cited by examiner

*Primary Examiner* — Allen C. Ho

(57) ABSTRACT

In one embodiment of the invention, a method for obtaining a tomogram of an anatomical structure is disclosed. In one step, an anatomical structure is scanned using a scanning source and a scanning detector. Both the scanning source and detector are connected to a gantry. In another step, the speed of the gantry is altered during the scanning process. Additionally or optionally the frame rate of the scan can be modified in such step. In a particular embodiment of the invention, the speed of the gantry is altered in synchronicity with the respiratory signal of a patient. Using such a method, a tomogram of an anatomical structure is obtained.

22 Claims, 5 Drawing Sheets

VARIABLE-SPEED COMPUTED TOMOGRAPHY SCANNING

FIELD OF THE INVENTION

The invention relates generally to medical diagnostic and treatment technology, and more specifically to computed tomography scanning for medical purposes.

BACKGROUND OF THE INVENTION

Advances in medical imaging technology have lead to significant improvements in the capability of medical professionals to diagnose and treat diseases. The battle against cancer has particularly benefited from these advances. Medical imaging improvements have made tumors more visible, and therefore have increased rates of early detection. In addition, many treatments for cancer—such as adaptive radiation therapy—require that a medical professional have highly accurate information regarding the location of a tumor in a patient's body so that radiation can be applied to minimize damage to healthy tissue while applying a concentrated dose of radiation to the tumor. Through both of these channels, advances in medical imaging technology have increased the medical community's ability to combat diseases such as cancer, and save lives.

Modern medical imaging traces its roots to the turn of the twentieth century with the production of the first x-ray radiograph. A traditional radiograph consists of a two-dimensional image of a scanned three-dimensional object. Such two-dimensional images can only provide information regarding a single layer of the scanned three-dimensional object. However, advances in the fields of computing and image processing have enabled medical imaging technology to advance to a stage where full three-dimensional representations of a scanned object can be obtained and utilized by a medical professional. The resultant three-dimensional representations are called tomograms, and they are produced from a large set of two-dimensional projections that are obtained and combined by a process called computed tomography scanning.

Computed tomography scanning involves the use of a scanning procedure that is conducted using a scanning source and a scanning detector that are dispersed on either side of a patient. Usually both the scanning source and scanning detector are mounted on the gantry of a medical imaging apparatus. Once scanning begins, the scanning source sends some form of detectable penetrating signal through the patient's body, and the resultant signal that is detected by the scanning detector provides information regarding the portion of the patient's body that is being scanned. This information is used to create a set of projections. After each projection is obtained, the gantry will change position slightly such that the scanning source and scanning detector are positioned relative the patient's body at a slightly different angle. In this manner, each new projection obtained provides additional information regarding the full tomogram of the object. The combined tomogram provides a large amount of information to a medical practitioner regarding the condition of the portion of the patient's body that was scanned such as the presence of tumors, potential blood clots, bone fractures, or other problematic conditions.

Applying a computed tomography scanning procedure to a moving anatomical structure greatly increases the complexity of the problem. As described above, the location of the scanning source and scanning detector are adjusted between the acquisition of each projection. If the anatomical structure is moving, it will change shape and position during this adjustment period, and the next acquisition will obtain a projection of a slightly different object. When the resultant projections are used to reconstruct a tomogram, the tomogram will be an amalgam of the anatomical structure in different configurations and it will not accurately represent the object as it exists in the desired configuration. The tomographic cross sections obtained when the structure was not in the desired configuration will create what are called artifacts in the image, which degrades the information content of the tomogram. This problem is particularly harmful in the field of lung cancer tumor detection given that the human lung moves and deforms dramatically during respiration.

One approach to obtaining a tomogram of a moving anatomical structure is called gated computed tomography scanning. The addition of the term "gated" is used to denote a family of approaches where either the number of projections chosen for reconstruction, or the number of projections taken as a whole are limited to produce a more accurate representation of the moving structure. One example of gated computed tomography scanning can be described with the assistance of FIG. 1. In this particular form of gated computed tomography, a marker is placed on the thorax of a patient which is used to track their breathing. From this marker, respiratory signal 100 is obtained. Axis 101 displays time, and axis 102 displays a patient's respiratory signal R(t), where the local maxima represent when a patient has fully inhaled and the local minima represent when a patient has fully exhaled. In accordance with this family of procedures, respiratory signal 100 will be used to gate the time periods when the structure is in a specific position and the projections are accepted, and when the structure is not in a specific position and they are rejected.

Referring again to FIG. 1, axis 111 tracks time on same scale as axis 101 and the Zero intercept of axis 111 With the zero intercept of axis 101. Axis 112 tracks the angle α at which the scanning apparatus is positioned at any time, while line 110 illustrates the angle α of a constant speed gantry. The gating aspect of these procedures manifests through the fact that the scanning source is turned on, or the projections are accepted for final use, only during the times covered by regions 120, 121, and 122. In this example signal 100 is gated by amplitude level 123. Therefore the gating windows span the time when the amplitude signal 100 exceeds level 123. This gating can also be done based on the phase of the respiratory signal. Level 123 is chosen such that the anatomical structure will alter the least during the gated period. For example, a human lung that is performing respiration will deform throughout the respiratory cycle except for a brief pause at the top and bottom of respiration. By only utilizing projections obtained in this window of minimal movement at the top or bottom of the cycle, artifacts caused by the movement of the object are mitigated.

The problem of gated scanning is not completely handled simply by rejecting projections during some phases of movement. If some projections are missing, their absence will also cause artifacts. Therefore artifacts caused by motion corrupted projections cannot be solved simply by discarding such projections. With reference again to FIG. 1, regions 130 are those in which projections were captured. No projections were obtained for the remainder of axis 112 outside those regions. Regions for which projections were obtained are called spokes, and regions where no projections were obtained are called sparses. Complex computer algorithms are capable of extrapolating sparses given enough spokes. Certain algorithms can also extrapolate the movement of the structure and potentially ignore gating altogether. However, these algorithms are not perfect and it is always better to obtain actual images.

There are several current approaches for dealing with spokes in gated computed tomography scanning. First, the gantry can be set to continue to spin through several rotations until all of the spokes are eliminated. However, because a person's respiratory signal is not perfectly uniform, there is no way to assure that the scanning apparatus will be aligned to the desired a when the respiratory signal is in a gated region. Furthermore, although clinical accuracy of the images is important, many forms of scanning sources emit radiation that is harmful to patients. Therefore, minimizing scanning times is extremely important. Another current approach involves instructing a patient to hold their breath, or breathe according to a preset pattern during a scan. Although this approach can eliminate the misalignment problem and assure that all of the spokes are eliminated, it may be difficult for a patient to maintain the required breathing pattern. Given that a patient undergoing this form of analysis may potentially be suffering from lung cancer it may be especially difficult for them to maintain a desired breathing pattern.

Solutions to the problem of producing a tomogram of a moving object using computed tomography scanning will benefit the field of medicine and various other fields. In particular, motion agnostic medical image screening for possible lung tumors is of critical importance given the fact that lung cancer is the most rampant killer of all forms of cancer in the world. Given that traditional computed tomography scanning required multiple images of an object from many different angles that cannot be taken simultaneously, the application of computed tomography scanning to lung cancer detection is highly problematic. Key advances in this field must address the production of images with high information content while limiting the amount of radiation to the scanned object without having to artificially adjust the object's natural movement.

SUMMARY OF INVENTION

In one embodiment of the invention, a method for obtaining a tomogram of a periodical moving anatomical structure is disclosed. In one step, an anatomical structure is scanned using a scanning source and a scanning detector. Both the scanning source and detector are connected to a gantry. In another step, the speed of the gantry is altered during the scanning process. In specific embodiments of the invention, the frame rate of the scan may optionally or additionally be modified during such steps. The speed of the gantry is altered such that the sampling rate used for the reconstruction of the tomographic volumes is optimized. Using such a method, a tomogram of an anatomical structure without motion artifacts is obtained.

DETAILED DESCRIPTION OF THE PREFERRED EMBODIMENTS

Figure 1:
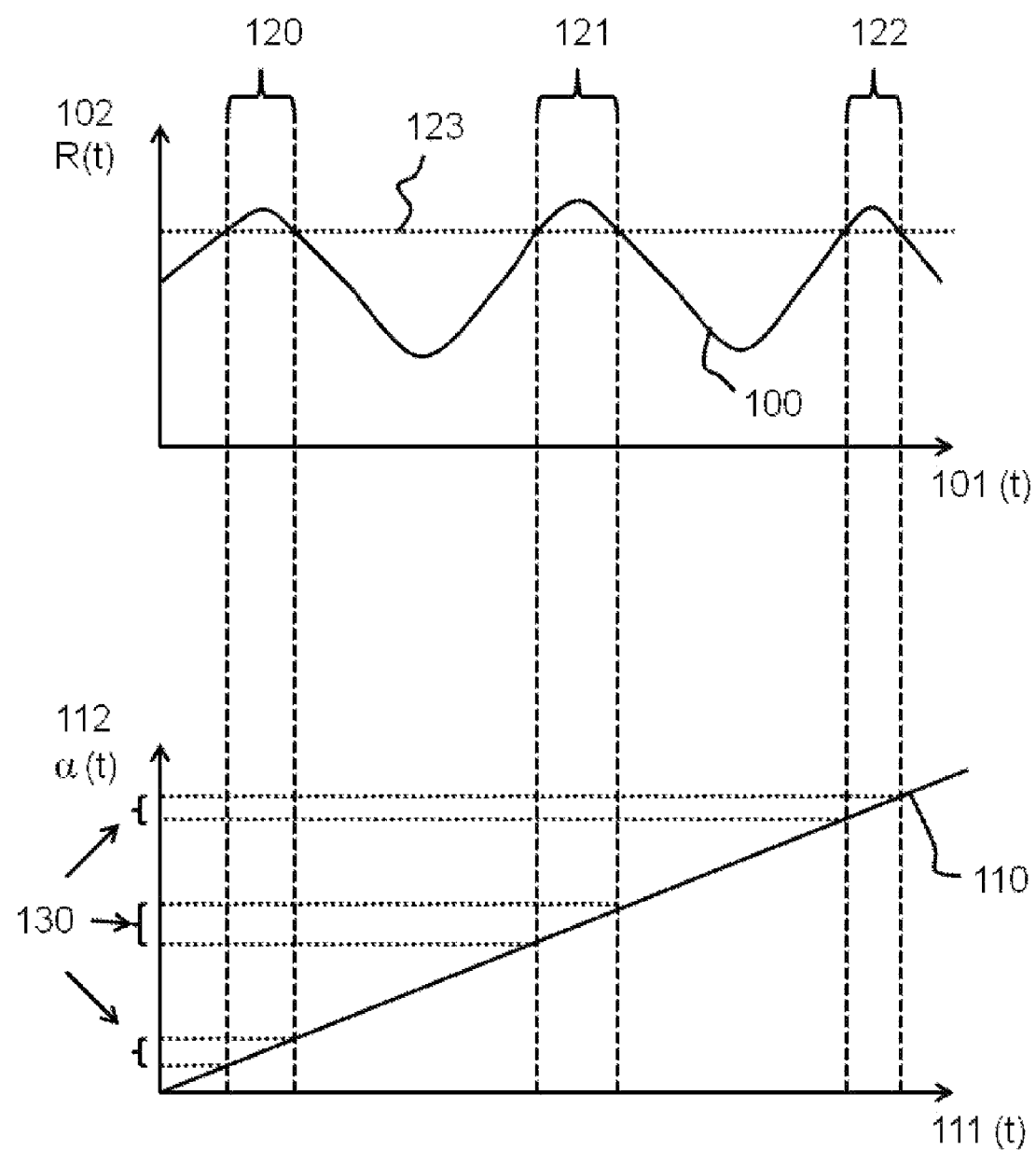
FIG. 1 illustrates a set of functions that describe how gated computed tomography scanning is used to scan an object in a manner that is in accordance with the prior art.

Reference will now be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the spirit and scope thereof. For instance, features illustrated or described as part of one embodiment may be used with another embodiment to yield a still further embodiment. Thus, it is intended that the present subject matter covers all modifications and variations within the scope of the appended claims and their equivalents.

Altering the speed of a scanning apparatus during the scanning phase of a computed tomography scan can greatly improve the accuracy of the resultant tomogram. Specific embodiments of the invention can produce a more accurate tomogram than can be produced without altering the speed of the scanning apparatus given the same amount exposure to scanning sources. In specific embodiments of the invention directed towards producing a tomogram of a structure exhibiting movement, the speed of the scanning apparatus is altered according to an observed periodic motion signal pattern exhibited by the scanned structure. In specific embodiments of the invention directed towards producing a tomogram of a respiring lung, the periodic motion signal is the respiratory signal of a patient. In other specific embodiments of the invention, the speed of the scanning apparatus is increased when the respiratory signal reaches a gated region, and decreases when the respiratory signal departs from the gated region. In this manner, the speed of the gantry is at a maximum during the gated region, and a minimum outside the gated region.

A method for obtaining a tomogram of an anatomical structure that is in accordance with the present invention can be described with reference to FIG. 2. In step 200, an anatomical structure is scanned using a scanning source and a scanning detector where the scanning source and detector are both connected to a gantry. In step 202, the speed of the gantry is altered during the scanning process. Additionally or alternatively, the frame rate of the scan could be altered during the scanning process. Such a modification can produce a similar result and it should be understood that such an option can be employed in other embodiments of the invention discussed herein. In specific embodiments of the invention, the decision for the degree of alteration that takes place in step 202 can be made in real time. This can be done through the use of a control circuit that constantly adjusts the gantry speed based on a non-deterministic input. Using the steps described above, a tomogram of a moving anatomical structure can be produced which has fewer artifacts than would have been produced in the absence of step 202.

A specific embodiment of the invention wherein a tomogram of a respiring anatomical structure such as a lung is obtained, can also be described with reference to FIG. 2. In step 201, a respiratory signal of the patient is monitored. This can be done using a marker placed on the thorax of the patient which is tracked by a camera. In other embodiments, the marker may contain a simple motion sensor or altimeter which tracks the patient's respiratory signal. The respiratory signal can also be monitored through the use of an implanted position marker such as those made by Calypso Medical Technologies, or Navotek Medical. The information obtained from the respiratory signal is then used to determine the degree to which the speed of the gantry is altered in step 202. This adjustment could be applied to the next cycle of the respiratory signal or it could be applied instantaneously.

Figure 2:
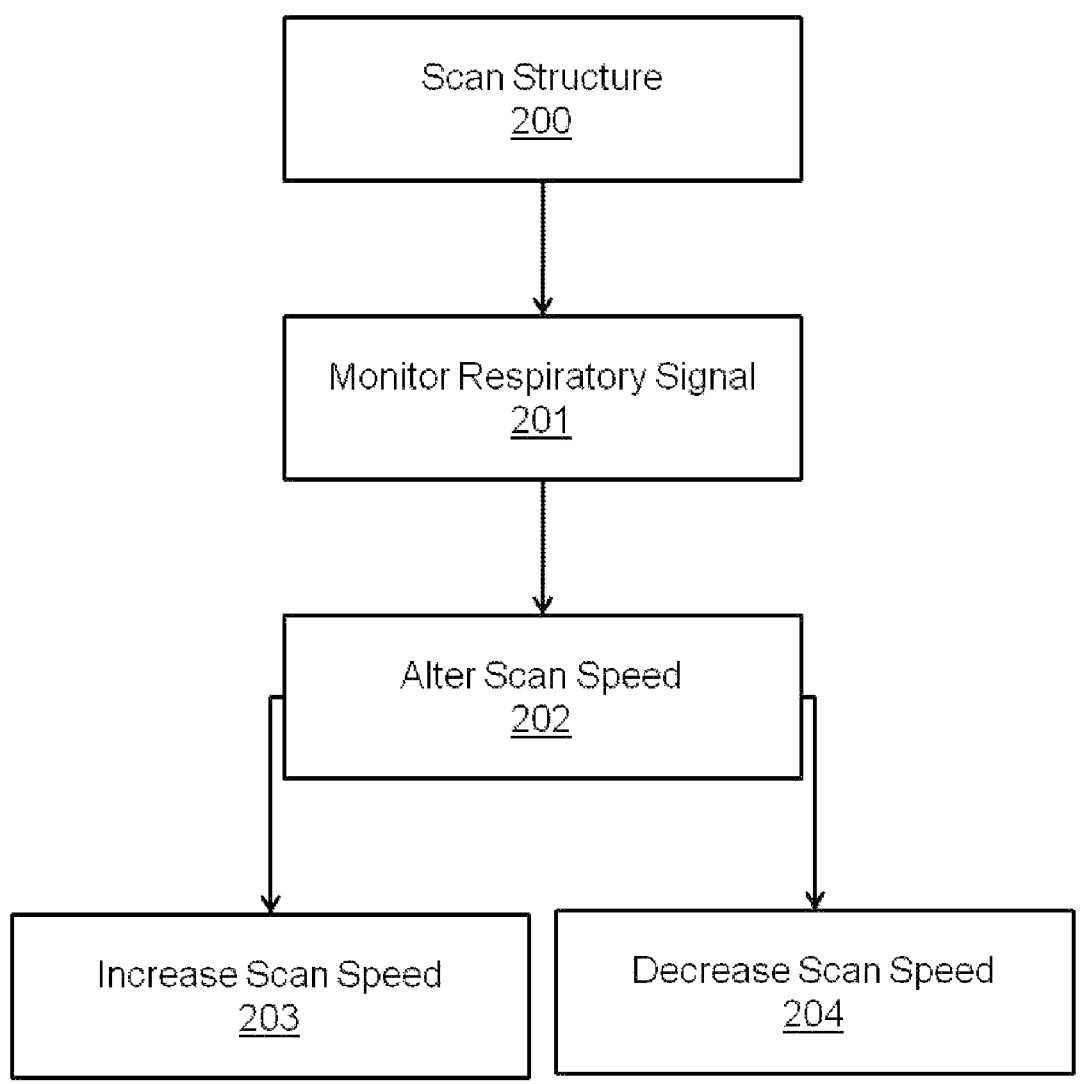
FIG. 2 illustrates a flow chart of a method for obtaining a tomogram of an anatomical structure that is in accordance with the present invention.

As shown in FIG. 2, the step of altering the speed of gantry can be broken out into two separate steps of the speed of the gantry 203 and decreasing the of the gantry 204. In specific embodiments of the invention, the respiratory signal is also used to determine a gating region for a gated computed tomography scan. The respiratory signal is therefore used to set the gating region of the scan and also the speed of the gantry and to do so in synchronicity. For example, as the gating region approaches, the speed of the gantry could be increased, and as the respiratory signal departs the gating region, the speed of the gantry could be decreased. Some of the benefits of this approach can described with reference to FIG. 4.

Figure 3:
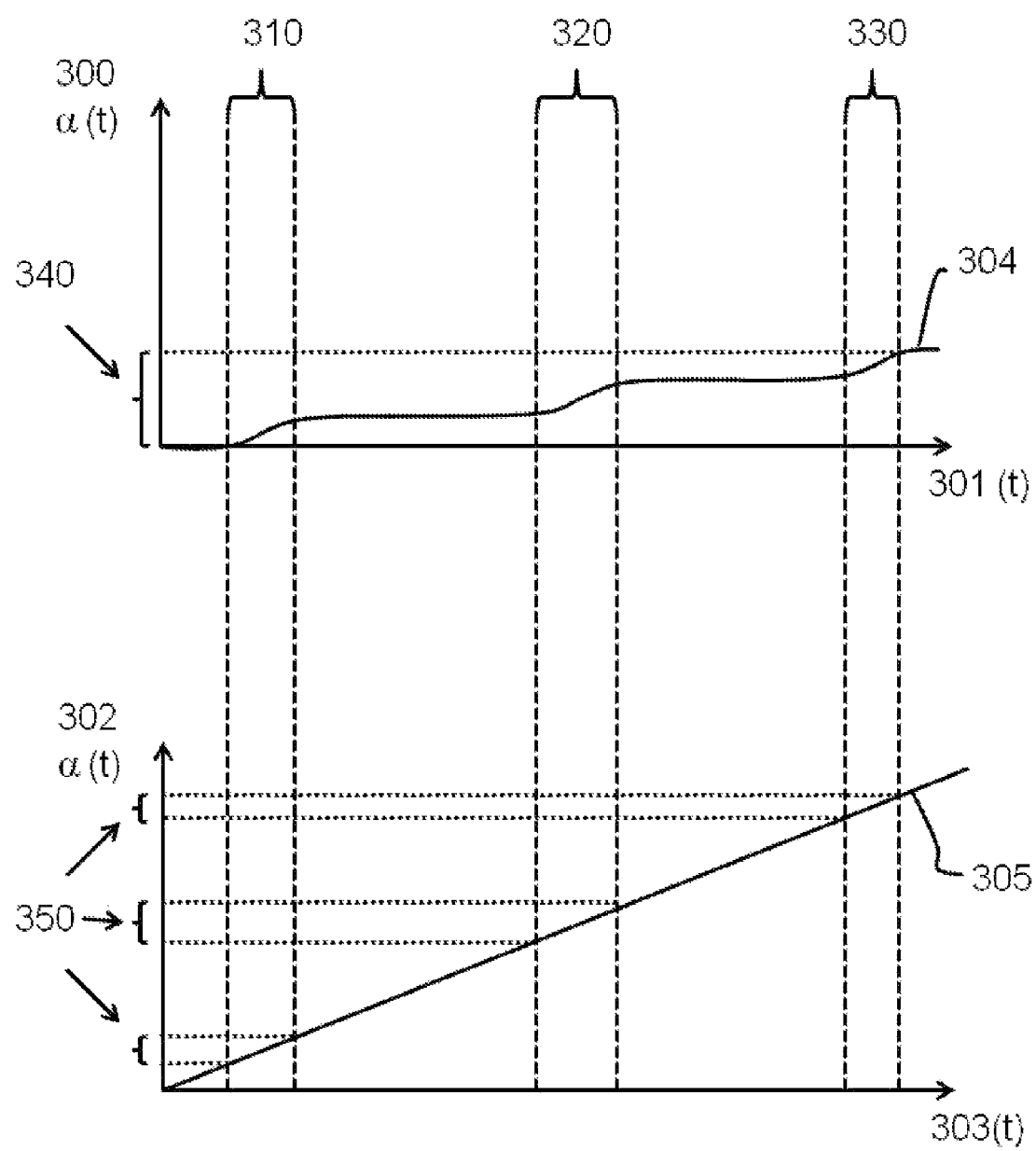
FIG. 3 illustrates a set of functions that describe an advantage for a computed tomography scan that is exhibited by specific embodiments of the present invention.

FIG. 3 displays two functions that contrast the amount of spokes and sparses in a computed tomography scan using a constant speed scan and a scan that is in accordance with the present invention. Axis 301 and axis 303 are in units of time, they have the same scale, and their zero-intercepts are equivalent. Axis 300 and axis 302 track the angle α of the gantry at a particular time similar to axis 112 in FIG. 1. Line 304 illustrates the angle α of a variable speed gantry while line 305 illustrates the angle α of a constant speed gantry. As with regions 120, 121, and 122 in FIG. 1, the times covered by region 310, 320, and 330 indicate when the scanning source is turned on, or the projections are accepted for final use. Regions 350 show the spokes of the constant speed gantry scan while the region marked by 340 shows the spokes of the variable speed gantry scan. Region 340 is shown as a solid block because non-idealities related to the time it takes for the gantry to slow down and speed up have been ignored and the movement of the gantry through the gated region has been maximized. Therefore it is assumed that the gantry speed is reduced to substantially zero outside the gating window and increases to its maximum scan speed during the gating window. For purposes of comparison the gantry's maximum scan speed is the same in both cases.

With reference to FIG. 3, it can be seen that the variable speed gantry will optimize a sampling rate of the scan. In a specific embodiment of the present invention, in a single gantry rotation the number of sparse regions of the scan will be minimized as compared to a constant speed scan. As the speed of the gantry and potentially the frame rate of the scan source are slowed when the object is not in the gating window, smaller sparse regions will be included in the overall scan obtained. Likewise, as the speed of the gantry and potentially the frame rate of the scan source are increased when the object is in the gating window, a bigger number of spokes will be obtained during the scan this will result in the desired decrease of the distance between spokes.

Referring again to FIG. 3, it can be seen that the variable speed gantry scan will in some embodiments complete a scan before the constant speed scan. As displayed, the constant speed gantry has already gone through a much larger a than the variable speed gantry. However, the constant speed gantry has missed several of the required projections necessary for a complete tomogram. If the constant speed scan is to obtain the missing projections it will need to continue rotating. Therefore, the fact that the variable speed scan pauses outside the gating window is not a drawback, and merely acts to ensure that no sparses are left behind. Although guided breathing may improve the performance of the constant speed scan, such techniques suffer from the drawbacks discussed above. This is because a respiratory signal is irregular and it is therefore extremely difficult to ensure that the constant speed gantry will be positioned at the proper angle during the gate window.

Embodiments of the present invention that exhibit the behavior described above are an improvement over the prior art because they are agnostic as to the relative distances and individual lengths of the gating periods. Therefore, they can optimally capture all of the required tomographic cross sections of the structure regardless of variations in the periodicity of the structure's movement. A related benefit for the specific situation of lung cancer screening is that a patient will be able to breathe normally and not have to match a predefined pattern during a scan.

Figure 4:
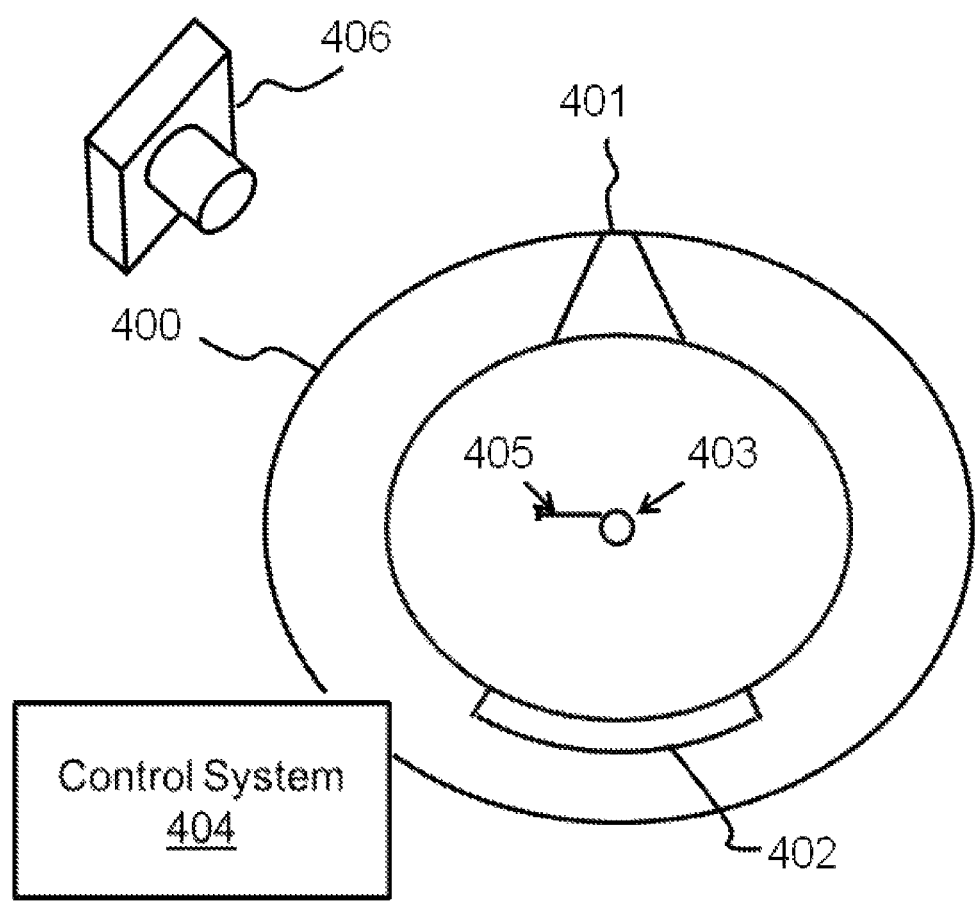
FIG. 4 illustrates a block diagram of a system that is in accordance with the present invention.

An apparatus for obtaining a tomogram of an anatomical structure that is in accordance with the present invention can be described with reference to FIG. 4. FIG. 4 displays gantry 400 having scanning source 401 and scanning detector 402 configured so that scanning signals from scanning source 401 can be detected by scanning detector 402 during a scan. In the specific embodiment displayed in FIG. 4, scanning detector 402, and scanning source 401 rotate around structure 403. Control system 404 is configured to engender gantry 400 with a desired speed and alter the speed of gantry 400 during a scan. In specific embodiments of the invention, control system 404 will alter the speed of gantry 400 according to the methods described above.

The apparatus described so far may optionally include a monitoring system 405 as displayed in FIG. 4. In a specific embodiment of the invention, the monitoring system 405 is configured to monitor the respiratory signal of a patient and communicate with control system 404. Control system 404 will then adjust the speed based on the information communicated from monitoring system 405 in accordance with the methods described above. In a specific embodiment of the invention, monitoring system 405 could be a marker attached to a patient including a simple motion sensor or altimeter and a wireless transmitter. In another specific embodiment of the invention, monitoring system 405 could be a position marker configured to be attached to a patient in combination with a camera 406 configured to monitor a location of the position marker. In another specific embodiment of the invention, monitoring system 405 can be an implanted position marker such as those made by Calypso Medical Technologies, or Navotek Medical.

Figure 5:
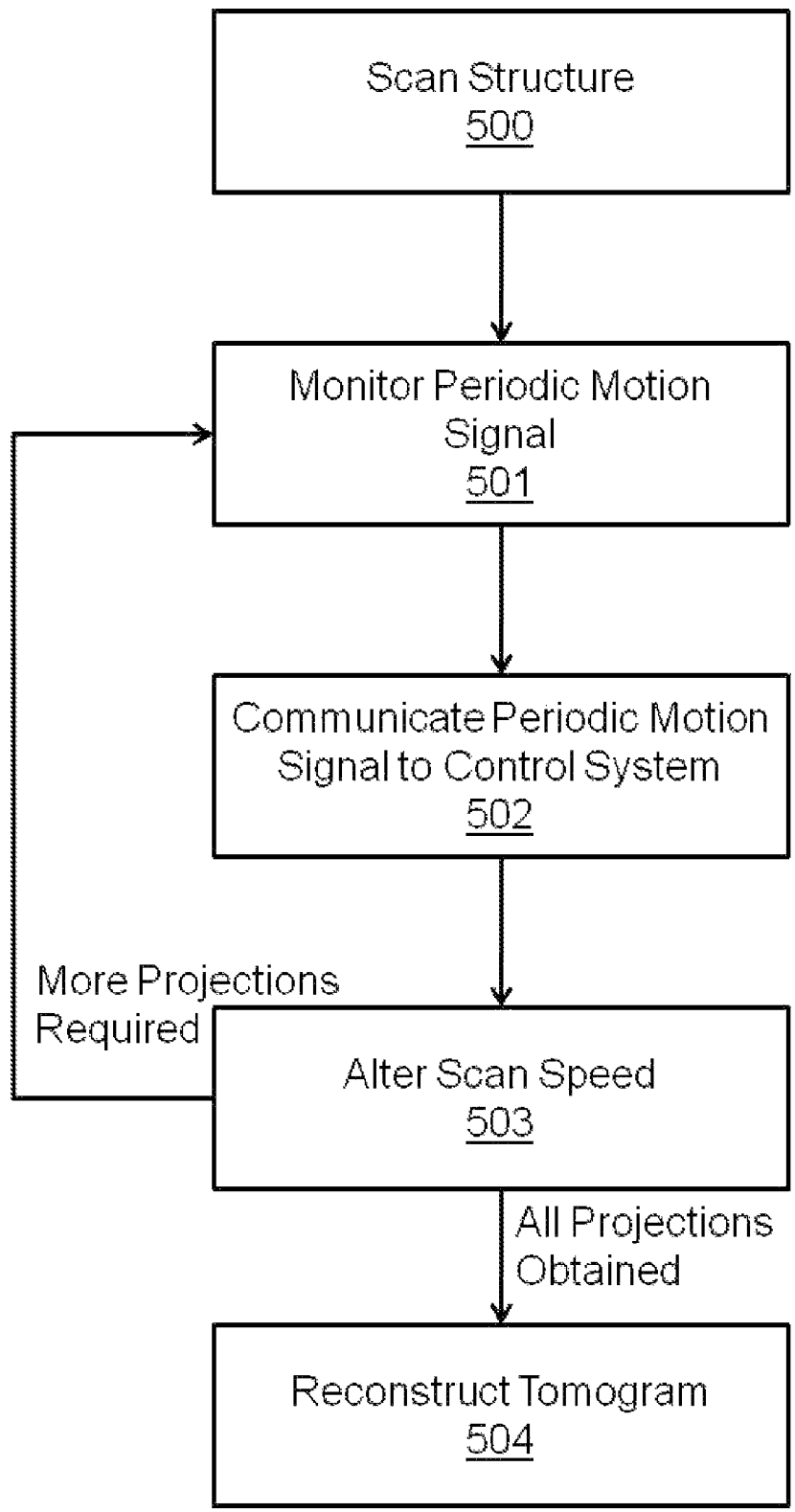
FIG. 5 illustrates a flow chart of a method for obtaining a tomogram of a structure that is in accordance with the present invention.

A method for obtaining a tomogram of a structure that is in accordance with the present invention can be described with reference to FIG. 5. In step 500 a structure is scanned using a scanning source and a scanning detector. The scanning source and scanning detector are connected to a gantry. In step 501, a periodic motion signal of the structure is monitored. In step 502, this periodic motion signal is communicated to a control system. In step 503, the speed of the gantry is altered using the control system while the structure is being scanned. The degree to which the speed is altered is based on information obtained from the periodic motion signal. In a specific embodiment of the invention, the speed of the gantry is altered in such a way that the sampling rate of the scan is optimized. In a specific embodiment of the invention, the speed of the gantry is altered in such a way that a set of sparse regions of the scan are reduced as compared to a set of sparse regions in a constant speed scan.

In a specific embodiment of the invention, step 501 through 503 can be repeated until all the necessary projections have been taken. In step 504, a tomogram is tomographically reconstructed using the set of projections produced during the scanning phase.

Although embodiments of the invention have been discussed primarily with respect to specific embodiments thereof, other variations are possible. Various configurations of the described system may be used in place of, or in addition to, the configurations presented herein. For example, although medical usage of the invention was discussed extensively in the application, the invention may be applied to many different fields including but not limited to non-destructive testing, security, and various other fields. The invention is not limited to use with any particular tomographic reconstruction algorithm, but instead can be aided by any form of complex algorithms or be designed to survive without them at all. Nothing in the disclosure should indicate that the invention is limited to a certain type of scanning technology. As described herein, altering the scan speed of the gantry includes reversing the direction of movement of the gantry which in some embodiments will allow tomographic cross sections to be obtained of the scanned structure that would otherwise have been missed. In addition, adjustments to the speed of the gantry do not have to be calculated and applied instantaneously as they can be calculated based off of information from prior cycles of the scanning process. Functions may be performed by hardware or software, as desired. In general, any of the presented diagrams are only intended to indicate one possible configuration, and many variations are possible. Those skilled in the art will also appreciate that methods and systems consistent with the present invention are suitable for use in a wide range of applications encompassing any form of tomogram production. While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those skilled in the art, without departing from the spirit and scope of the present invention, which is more particularly set forth in the appended claims. Furthermore, those skilled in the art will appreciate that the foregoing description is by way of example only, and is not intended to limit the invention.

What is claimed is:

1. A method for obtaining a tomogram of an anatomical structure comprising the steps of:
    monitoring a periodic motion signal of said anatomical structure;
    determining a plurality of intervals indicative of a position of said anatomical structure based on said periodic motion signal;
    scanning said anatomical structure using a scanning source and a scanning detector at a scanning frame rate, said scanning source and said scanning detector being coupled to a gantry; and
    altering a speed of said gantry during said scanning to be synchronized with said plurality of intervals such that said speed of said gantry is substantially decreased as said periodic motion signal leaves said plurality of intervals and is substantially increased as said periodic motion signal approaches said plurality of intervals; and
    adjusting a speed of said scanning frame rate to be synchronized with said plurality of intervals such that said scanning frame rate is increased when said periodic motion signal is inside said plurality of intervals and decreased when said periodic motion signal is outside said plurality of intervals.

2. The method from claim 1, wherein said altering comprises determining a degree of alteration in real time.

3. The method from claim 1, wherein said monitored periodic motion signal comprises a respiratory signal of a patient;
    wherein said altering said speed of said gantry comprises determining a degree of alteration used during said altering based on a first quantum of information from said respiratory signal.

4. The method from claim 3, wherein said adjusting said scanning frame rate comprises determining a degree of adjustment of said scanning frame rate based on a second quantum of information from said respiratory signal.

5. The method from claim 3, wherein:
    said degree of alteration is selected for a scan that is commensurate with a current cycle of said respiratory signal; and
    said first quantum of information is obtained from a prior cycle of said respiratory signal.

6. The method from claim 5, wherein said altering further comprises decreasing said speed of said gantry and said scanning rate substantially to zero when said respiratory signal departs an interval corresponding to said respiratory signal.

7. The method from claim 6 further comprising reversing a direction of movement of said gantry when said respiratory signal departs said interval corresponding to said respiratory signal.

8. The method from claim 1, wherein altering a speed of said gantry and said scanning frame rate during said scanning comprises maintaining said speed of said gantry and said scanning frame rate to a maximum possible speed when said periodic motion signal is inside of said plurality of intervals.

9. The method from claim 1, wherein said speed of said gantry is decreased to substantially zero when said periodic motion signal is outside said plurality of intervals.

10. An apparatus for obtaining a tomogram of an anatomical structure comprising:
    a gantry having a scanning source and a scanning detector, said scanning source and said scanning detector configured such that scanning signals from said scanning source can be detected by said scanning detector during a scan at a scanning frame rate, said scan being capable of being used to produce a tomogram; and
    a control system configured to engender said gantry with a desired speed and to alter said desired speed during said scan such that a size of sparses in said scan is reduced as compared to a second size of said sparses in said scan that would have resulted from an otherwise equivalent constant speed scan,
    wherein said speed of said gantry is synchronized with a plurality of intervals indicative of a position of said anatomical structure during a periodic motion signal by said control system such that said speed of said gantry is substantially decreased as said periodic motion signal leaves said plurality of intervals and is substantially increased as said periodic motion signal approaches said plurality of intervals,
    further wherein a scanning frame rate is synchronized by said control system with said plurality of intervals such that said scanning frame rate is increased when said periodic motion signal is inside said plurality of intervals and decreased when said periodic motion signal is outside said plurality of intervals.

11. The apparatus from claim 10, wherein said control system is configured to select said desired speed in real time.

12. The apparatus from claim 11, wherein said control system is configured to modify said scanning frame rate to be synchronized with said plurality of intervals such that said scanning frame rate is paused when said periodic motion signal is outside said plurality of intervals.

13. The apparatus from claim 10, wherein said periodic motion signal comprises a respiratory signal of a patient, and wherein said apparatus further comprises a monitoring system configured to monitor said respiratory signal of said patient and communicate with said control system, wherein said control system is configured to select said desired speed based on a quantum of information from said respiratory signal.

14. The apparatus from claim 13, said monitoring system further comprising:
a position marker configured to change position to correspond to a movement of said patient; and
a camera configured to monitor a location of said position marker.

15. The apparatus from claim 14, wherein:
said control system is configured to select said desired speed for a current cycle; and
said quantum of information is obtained from a prior cycle of said respiratory signal.

16. The apparatus from claim 15, wherein said control system is configured to decrease said desired speed substantially to zero after said respiratory signal passes through an interval corresponding to said respiratory signal.

17. The apparatus from claim 16, wherein said control system is configured to reverse a direction of movement of said gantry when said respiratory signal departs said interval corresponding to said respiratory signal.

18. The apparatus from claim 14, wherein said position marker comprises at least one of:
a position marker disposed on top of a portion of said patient;
a position marker implanted in said patient; and
an altimeter.

19. The apparatus from claim 13, said monitoring system further comprising an implanted position marker.

20. A method for obtaining a tomogram of an anatomical structure comprising the steps of:
scanning said anatomical structure using a scanning source and a scanning detector, said scanning source and said scanning detector being connected to a gantry;
monitoring a periodic motion signal of said anatomical structure;
communicating said periodic motion signal to a control system;
altering a speed of said gantry using said control system during said scanning based on a quantum of information from said periodic motion signal, said quantum of information comprising a plurality of intervals indicative of a position of said anatomical structure, wherein said altering said speed of said gantry comprises synchronizing said speed of said gantry and said a scanning frame rate with said plurality of intervals such that said speed of said gantry is substantially decreased as said periodic motion signal leaves said plurality of intervals and is substantially increased as said periodic motion signal approaches said plurality of intervals,
reconstructing said tomogram using a set of projections produced during said scanning,
wherein said altering comprises reducing a set of sparse regions inherent to said scanning as compared to a second set of sparse regions that would have been inherent to said scanning if said scanning had been conducted using an otherwise equivalent constant speed scan,
wherein said synchronizing comprises adjusting said scanning frame rate such that said scanning frame rate is increased when said periodic motion signal is inside said plurality of intervals and decreased when said periodic motion signal is outside said plurality of intervals.

21. The method from claim 20, said altering further comprising the steps of:
increasing said speed when said periodic motion signal approaches an interval of said periodic motion signal; and
decreasing said speed substantially to zero when said periodic motion signal departs said interval of said periodic motion signal.

22. The method from claim 21, further comprising the step of reversing a direction of movement of said gantry when said periodic motion signal departs said interval of said periodic motion signal.

* * * * *